(12) United States Patent
Adachi et al.

(10) Patent No.: US 7,915,041 B2
(45) Date of Patent: Mar. 29, 2011

(54) HYBRIDOMA CAPABLE OF PRODUCING ANTI-DECTIN-1 MONOCLONAL ANTIBODY

(75) Inventors: Yoshiyuki Adachi, Tokyo (JP); Naohito Ohno, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 793 days.

(21) Appl. No.: 11/719,245

(22) PCT Filed: Jun. 30, 2005

(86) PCT No.: PCT/JP2005/012098
§ 371 (c)(1),
(2), (4) Date: May 14, 2007

(87) PCT Pub. No.: WO2006/051632
PCT Pub. Date: May 18, 2006

(65) Prior Publication Data
US 2009/0291459 A1 Nov. 26, 2009

(30) Foreign Application Priority Data

Nov. 12, 2004 (JP) ................................ 2004-329795
Nov. 12, 2004 (JP) ................................ 2004-329796
Nov. 12, 2004 (JP) ................................ 2004-329797

(51) Int. Cl.
*C12N 5/07* (2010.01)
*C12N 5/16* (2006.01)
*C12P 21/08* (2006.01)
*C07K 16/00* (2006.01)

(52) U.S. Cl. .................................... 435/343; 530/388.7
(58) Field of Classification Search .................. None
See application file for complete search history.

(56) References Cited

U.S. PATENT DOCUMENTS 6,046,158 A 4/2000 Ariizumi et al.

FOREIGN PATENT DOCUMENTS

WO 02/096945 A2 12/2002

OTHER PUBLICATIONS

Adachi Yoshiyuki, et al., Characterization of beta-glucan recognition site on C-type lectin, dectin 1., Infection and Immunity. Jul. 2004, vol. 72 No. 7, pp. 4159 to 4171.
Brown, Gordon D. et al., Dectin-1 is a major beta-glucan receptor on macrophages., The Journal of Experimental Medicine. 2002, vol. 196 No. 3, pp. 407 to 412.
Edited by Yukio Sugino, "Bio Technology Seriese Monoclonal Kotai", Kodansha Ltd., Mar. 10, 1986, pp. 10-11.
Supplementary European Search Report dated Jun. 18, 2008.
Gordon D. Brown, et al., A new receptor for B-glucans, Nature, vol. 413, 36-37 (2001).
Phillip R. Taylor, et al., The B-Glucan Receptor, Dectin-1, Is Predominantly Expressed on the Surface of Cells of the Monocyte/Macrophage and Neutrophil Lineages, Journal of Immunology, vol. 169, pp. 3876-3882 (2002).
Kiyoshi Ariizumi, et al., Identification of a Novel, Dendritic Cell-associated Molecule, Dectin-1, by Subtractive cDNA Cloning, The Journal of Biological Chemistry, vol. 275, pp. 20157-20167 (2000).
International Preliminary Examination Report, May 24, 2007.
Extended European Search Report issued in European Patent Application No. 09158699.0-2402, dated Aug. 11, 2009.
Janet A. Willment, et al.; "The human β-glucan receptor is widely expressed and functionally equivalent to murine Dectin-1 on primary cells"; European Journal of Immunology, Wiley-VCH Verlag GMBH & Co. KGaA; vol. 35, No. 5; May 1, 2005; pp. 1539-1547; XP002412179.

*Primary Examiner* — Amy E Juedes
(74) *Attorney, Agent, or Firm* — Sughrue Mion, PLLC

(57) ABSTRACT

A hybridoma capable of producing a monoclonal antibody against dectin-1, and a monoclonal antibody which specifically reacts with dectin-1.

4 Claims, 1 Drawing Sheet

HYBRIDOMA CAPABLE OF PRODUCING ANTI-DECTIN-1 MONOCLONAL ANTIBODY

TECHNICAL FIELD

The present invention relates to a novel hybridoma capable of producing a monoclonal antibody against dectin-1 and the like.

BACKGROUND ART

Firstly, the abbreviations used in the present application are described.
BG: (1→3)-β-D-glucan
CRD: Carbohydrate recognition domain
FACS: Fluorescence-activated cell sorter
PBS: Phosphate-buffered saline
PCR: Polymerase chain reaction
SDS-PAGE: Sodium dodecyl sulfate-polyacrylamide gel electrophoresis
SPG: Schizophyllan (1,6-branched BG having a triple helix structure, derived from *Schizophyllum commune*)

Dectin-1 is a specific receptor for (1→3)-β-D-glucans and present on the cell surface of leukocytes such as neutrophil, macrophage and dendritic cell (cf., Non-patent references 1 and 2).

Conventionally, an antiserum for dectin-1 has been reported (Non-patent reference 3), but there are no reports on a monoclonal antibody for this.

Non-patent reference 1: Brown, G. et al., *Nature*, vol. 413, p. 36-37, 2001
Non-patent reference 2: Taylor P. R. et al., *Journal of Immunology*, vol. 169, p. 3876-3882, 2002
Non-patent reference 3: Ariizumi, K. et al., *The Journal of Biological Chemistry*, vol. 275, no. 26, p. 20157-20167, 2000

DISCLOSURE OF THE INVENTION

Problems to be Solved by the Invention

Objects of the present invention are to provide a novel hybridoma capable of producing a monoclonal antibody against dectin-1, a novel anti-dectin-1 antibody produced by the hybridoma, a novel process for producing the anti-dectin-1 antibody using the above-described hybridoma and a novel method for detecting dectin-1 using the above-described antibody.

Means for Solving the Problems

In order to solve the above-described problems, the inventors of the present invention have conducted intensive studies and, as a result, provided a novel hybridoma capable of producing a monoclonal antibody against dectin-1, a novel anti-dectin-1 antibody produced by the hybridoma, a novel process for producing the anti-dectin-1 antibody using the above-described hybridoma and a novel method for detecting dectin-1 using the above-described antibody to thereby have accomplished the present invention.

That is, the present invention relates to the following (1) to (6).
(1) A hybridoma capable of producing a monoclonal antibody against dectin-1 (hereinafter referred to as "hybridoma of the present invention").
(2) The hybridoma according to (1), which is a hybridoma having a deposit number of FERM BP-10151, a hybridoma having a deposit number of FERM BP-10153 or a hybridoma having a deposit number of FERM BP-10152.
(3) A monoclonal antibody which specifically reacts with dectin-1.
(4) A monoclonal antibody against dectin-1, which is produced by the hybridoma according to (1) or (2) (hereinafter (3) and (4) are referred to as "antibody of the present invention").
(5) A process for producing a monoclonal antibody against dectin-1, which comprises culturing the hybridoma according to (1) or (2) and recovering the monoclonal antibody against dectin-1 from the culture (hereinafter referred to as "production process of the present invention").
(6) A method for detecting dectin-1, which comprises reacting the monoclonal antibody according to (3) or (4) with dectin-1 (hereinafter referred to as "detection method of the present invention").

Effect of the Invention

The hybridoma of the present invention is markedly useful, because it can be used as a tool that can produce an antibody against dectin-1 uniformly, massively, permanently and inexpensively. The antibody of the present invention is a novel monoclonal antibody against dectin-1 and is markedly useful. Also, according to the production process of the present invention, the antibody of the present invention can be produced uniformly and in a large amount, so that this is markedly useful. In addition, according to the detection method of the present invention, dectin-1 can be detected conveniently, quickly, specifically, with high sensitivity and high accuracy, and inexpensively, so that this is markedly useful.

BEST MODE FOR CARRYING OUT THE INVENTION

Figure 1:
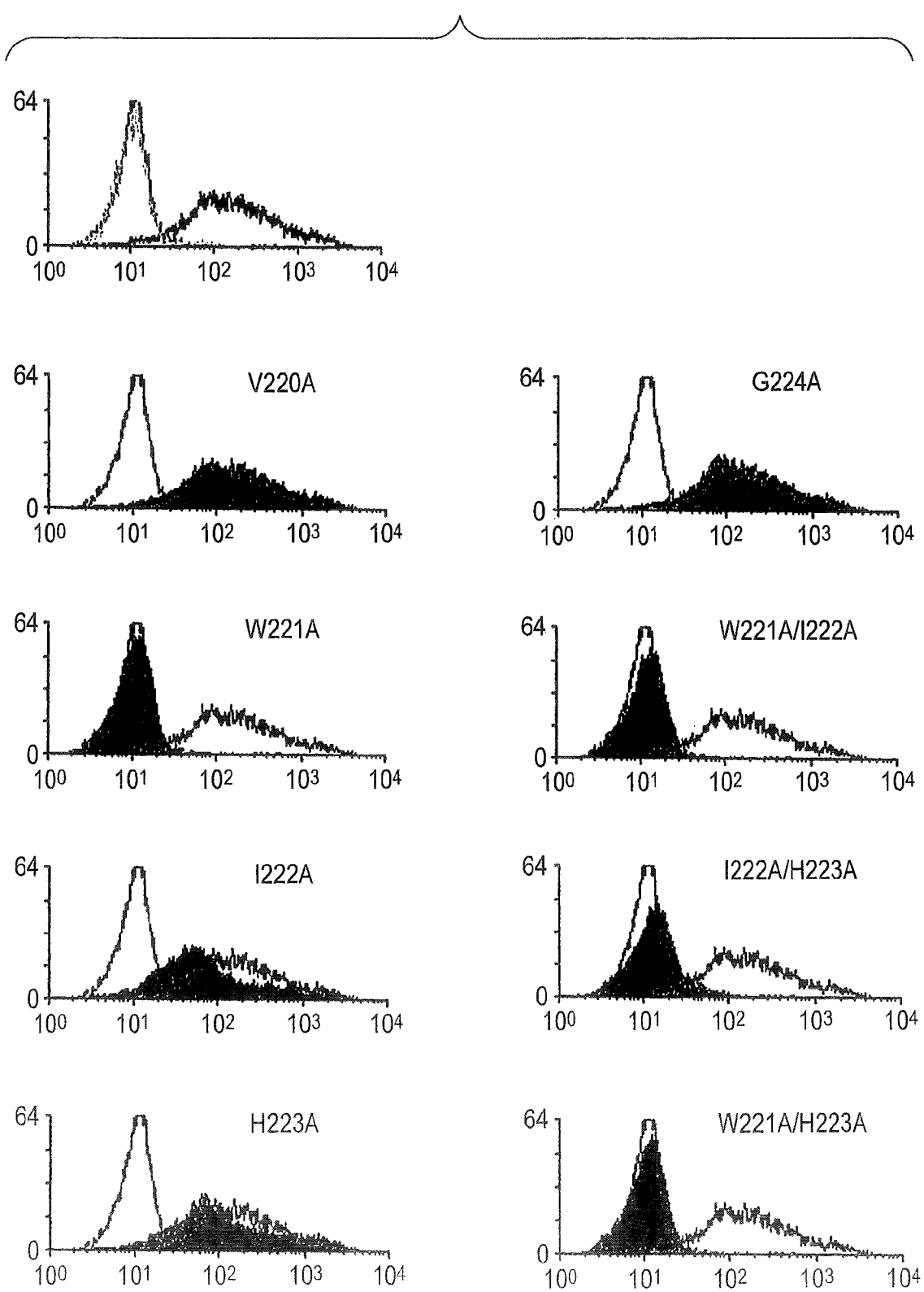
FIG. 1 is a graph showing binding of 4B2 to dectin-1 or mutants thereof.

The present invention is described below in detail based on the best mode for carrying out the present invention.
<1> Hybridoma of the Present Invention The hybridoma of the present invention can be obtained by immunizing an immune animal such as rat, mouse, guinea pig, rabbit, goat, sheep, horse, pig, dog, cat or domestic fowl with dectin-1 or a partial peptide thereof as the immunogen, recovering an antibody producer cell from lymph node, spleen, peripheral blood or the like of the immunized animal, preparing hybridomas by carrying out cell fusion of the antibody producer cell with a myeloma cell of mouse, rat, guinea pig, rabbit, goat, sheep, horse, pig, dog, cat, domestic fowl or the like, and selecting a hybridoma which produces a monoclonal antibody that reacts specifically with dectin-1.

Examples of the hybridoma of the present invention include a hybridoma having a deposit number of FERM BP-10151 (hereinafter referred to as "hybridoma-1 of the present invention"), a hybridoma having a deposit number of FERM BP-10153 (hereinafter referred to as "hybridoma-2 of the present invention"), a hybridoma having a deposit number of FERM BP-10152 (hereinafter referred to as "hybridoma-3 of the present invention") and the like.

The hybridoma-1 of the present invention, obtained by carrying out cell fusion of a mouse myeloma cell with a rat lymphoid cell, has been received as a microorganism having indication for identification used by the depositor "Mouse- Rat hybridoma 4B2", on Oct. 22, 2004, as deposit number FERM BP-10151 by International Patent Organism Depositary, National Institute of Advanced Industrial Science and Technology, Central 6, 1-1-1, Higashi Tsukuba, Ibaraki, 305-8566 JAPAN. Accordingly, the hybridoma of the present invention can be obtained from the depositary.

The hybridoma-2 of the present invention, obtained by carrying out cell fusion of a mouse myeloma cell with a rat lymphoid cell, has been received as a microorganism having indication for identification used by the depositor "Mouse-Rat hybridoma RH1", on Oct. 22, 2004, as deposit number FERM BP-10153 by International Patent Organism Depositary, National Institute of Advanced Industrial Science and Technology, Central 6, 1-1-1, Higashi Tsukuba, Ibaraki, 305-8566 JAPAN. Accordingly, the hybridoma of the present invention can be obtained from the depositary.

The hybridoma-3 of the present invention, obtained by carrying out cell fusion of a mouse myeloma cell with a rat lymphoid cell, has been received as a microorganism having indication for identification used by the depositor "Mouse-Rat hybridoma SC30", on Oct. 22, 2004, as deposit number FERM BP-10152 by International Patent Organism Depositary, National Institute of Advanced Industrial Science and Technology, Central 6, 1-1-1, Higashi Tsukuba, Ibaraki, 305-8566 JAPAN. Accordingly, the hybridoma of the present invention can be obtained from the depositary.

The hybridoma of the present invention can be handled in accordance with the general culturing and preservation methods and the like of antibody producer hybridomas. Regarding the details, see the item "<3> Production process of the present invention" which is described later.

Since the hybridoma of the present invention produces the antibody of the present invention, it can be used for the production of the antibody of the present invention and the like.

<2> Antibody of the Present Invention

The antibody of the present invention is a monoclonal antibody which specifically reacts with dectin-1, and is preferably an anti-dectin-1 monoclonal antibody produced by the hybridoma of the present invention. Examples of the antibody of the present invention include a monoclonal antibody against dectin-1 produced by the hybridoma-1 of the present invention (hereinafter referred to as "antibody-1 of the present invention"), a monoclonal antibody against dectin-1 produced by the hybridoma-2 of the present invention (hereinafter referred to as "antibody-2 of the present invention"), a monoclonal antibody against dectin-1 produced by the hybridoma-3 of the present invention (hereinafter referred to as "antibody-3 of the present invention") and the like.

The hybridomas of the present invention are described above.

The antibody-1 of the present invention is a rat immunoglobulin G2a/κ (IgG2a/κ) which binds to dectin-1. The dectin-1 to which the antibody-1 of the present invention binds is preferably derived from a mouse.

The antibody-2 of the present invention is a rat immunoglobulin G1/κ (IgG1/κ) which binds to dectin-1. The dectin-1 to which the antibody-2 of the present invention binds is preferably derived from a mouse.

The antibody-3 of the present invention is a rat immunoglobulin G2a/κ (IgG2a/κ) which binds to dectin-1. The dectin-1 to which the antibody-3 of the present invention binds is preferably derived from a mouse.

In addition, the antibodies 1 and 2 of the present invention are characterized in that they have activity of inhibiting binding of BG (particularly SPG or zymosan) to dectin-1. Based on this, it can be considered that the epitopes of the antibodies 1 and 2 of the present invention with BG (particularly SPG or zymosan) in the dectin-1 molecule are common to each other.

Also, the antibody-3 of the present invention is characterized in that it does not inhibit binding of BG (particularly SPG or zymosan) to dectin-1. Based on this, it can be considered that the epitopes of the antibody-3 of the present invention with BG (particularly SPG or zymosan) in the dectin-1 molecule are common to each other.

In addition, it is also characterized in that at least tryptophan at position 221 in the mouse-derived dectin-1 and its peripheral amino acid residues are essential for the binding of the antibody-1 of the present invention to dectin-1.

Not only the antibody itself produced by the hybridoma of the present invention, but also a product of the antibody labeled by a conventionally known method, the antibody immobilized on an insoluble carrier, etc., and the like can also be included in the antibody of the present invention.

The substance which can be used for the labeling of the antibody of the present invention is not particularly limited, so long as it can be used for the labeling of general protein, and its examples include an enzyme (peroxidase, alkaline phosphatase, β-galactosidase, luciferase, acetylcholine esterase, glucose oxidase or the like), a radioisotope ($^{125}$I, $^{131}$I, $^{3}$H or the like), a fluorescence dye (Alexa Fluor (registered trademark) 488, fluorescein isothiocyanate (FITC), 7-amino-4-methylcoumarin-3-acetic acid (AMCA), dichlorotriadinylaminofluorescein (DTAF), tetramethylrodamine isothiocyanate (TRITC), Lissamine Rhodamine B, Texas Red, Phycoerythrin PE), umbelliferone, europium, phycocyanin, tricolor, cyanin or the like), a chemiluminescent material (luminol or the like), a hapten (dinitrofluorobenzene, adenosine monophosphate (AMP), 2,4-dinitroaniline or the like), either one part of a specific binding pair (biotin and avidins (streptoavidin or the like), lectin and a sugar chain, an agonist and a receptor of the agonist, heparin and antithrombin III (ATIII), a polysaccharide and its binding protein (hyaluronic acid and hyaluronic acid binding protein (HABP) or the like) and the like.

The method for labeling the antibody with such a substance can be optionally selected from conventionally known methods suitable for respective substances, such as a glutaraldehyde method, a periodate crosslinking method, a maleimide crosslinking method, a carbodiimide method, an activated ester method and the like when labeled with an enzyme, a chloramines T method, a lactoperoxidase method and the like when labeled with a radioisotope (cf., *Second Series Biochemistry Experimentation Course* 2 "Chemistry of Protein (the last volume)") edited by Tokyo Kagaku Dojin (1987) and the like. For example, when biotin is used as the labeling substance, a method using an N-hydroxy succinimide ester derivative or hydrazide derivative of biotin (cf., *Avidin-Biotin Chemistry: A Handbook*, p. 57-63, published in 1994 by PIERCE CHEMICAL COMPANY) and the like can be used.

Examples of the shape of the insoluble carrier on which an antibody produced by the hybridoma of the present invention can be immobilized include a plate (e.g., each welt of a microplate or the like), a tube, beads, a membrane, a gel, a particulate solid carrier (synthetic polymer particles such as gelatin particles, kaolin particles, or a latex, or the like) and the like. In addition, examples of the material of such a carrier include polystyrene, polypropylene, polyvinyl chloride, nitrocellulose, nylon, polyacrylamide, Teflon (registered trademark), polyallomer, polyethylene, glass, agarose and the like.

As the method for immobilizing an antibody produced by the hybridoma of the present invention on such an insoluble carrier, generally known methods such as a physical adsorption method, a covalent bond method and an inclusion method as immobilized enzyme preparation methods (cf., *Immobilized Enzyme*, 1975, published by Kodansha, pp. 9-75) can be applied.

In addition, those in which an antibody produced by the hybridoma of the present invention is made into an Fab-containing fragment or the like by its treatment with a protease which does not degrade antigen binding site (Fab) (e.g., plasmin, pepsin, papain or the like) are also included in the antibody of the present invention. Examples of the Fab-containing antibody fragment include Fabc, (Fab')$_2$ and the like in addition to Fab.

The antibody of the present invention can be produced by culturing the hybridoma of the present invention, and recovering a monoclonal antibody against dectin-1 from the culture. See the item of the following "<3> Production process of the present invention" for its details.

However, the production process of the antibody of the present invention is not limited to this, and other production process, such as a method in which it is produced by a genetic engineering means based on the base sequence information of a gene encoding the antibody of the present invention or the amino acid sequence information of the antibody of the present invention, and the like may be employed.

In addition, the antibody of the present invention may be in the completely purified state, partially purified state or unpurified state.

Whether or not the produced antibody binds to dectin-1, or specifically binds thereto, and the like can be easily determined by those skilled in the art by general methods using dectin-1, other substance which becomes the antigen (e.g., other kind of protein) and the like.

In addition, when the antibody of the present invention is preserved, distributed, used, for example, other components may be contained therein, so long as the function and activity of the antibody of the present invention are not substantially spoiled. For example, excipients, buffers, stabilizers, preservatives and the like which are generally used in preparing reagents can be contained therein. Such components include, for example, phosphate buffered saline (PBS), sodium azide (NaN$_3$), bovine serum albumin (BSA) and the like.

The antibody of the present invention can be used for the detection, measurement and affinity purification of dectin-1 and other purposes.

<3> Production Process of the Present Invention

The production process of the present invention is a process for producing a monoclonal antibody against dectin-1, which comprises culturing the hybridoma of the present invention and recovering the monoclonal antibody against dectin-1 from the culture.

The hybridoma of the present invention is as described above.

Specific culturing method and culturing conditions for the hybridoma of the present invention are not particularly limited, so long as the hybridoma produces the antibody of the present invention. For example, the hybridoma of the present invention can be cultured in a liquid medium in which about 10% of fetal bovine serum or the like is contained in a medium generally used for the culturing of a hybridoma (e.g., RPMI 1640 (manufactured by Sigma) or the like). In this case, in order to prevent microbial contamination, antibiotics such as gentamicin may be further contained.

The conditions in culturing the hybridoma of the present invention in such a liquid medium are not particularly limited too, so long as the hybridoma produces the antibody of the present invention, but the hybridoma of the present invention to be inoculated into the liquid medium is preferably 1 to $2\times10^5$ cells/ml or more. Also, the culturing temperature is preferably about 37° C. In addition, the carbon dioxide concentration in carrying out the culturing is preferably about 5% (v/v).

In addition, the hybridoma of the present invention can also be cultured in the living body such as the abdominal cavity of a mouse. In this case, the living body can be reared under such conditions that the living body which keeps the hybridoma of the present invention can survive.

By culturing the hybridoma of the present invention in this manner, a monoclonal antibody against dectin-1 is produced by the hybridoma of the present invention, and the monoclonal antibody against dectin-1 is accumulated in the culture. In this connection, the term "culture" as used in the present application means a fraction which contains the monoclonal antibody against dectin-1 produced by the hybridoma of the present invention, and the hybridoma after the culturing, the medium after the culturing, a mixture of both of them and ascites (when the hybridoma of the present invention was cultured in the living body) and the like are included therein. Particularly, the culture is preferably "medium after the culturing" or "ascites (when the hybridoma of the present invention was cultured in the living body)". That is, the production process of the present invention preferably further comprises, after culturing of the hybridoma of the present invention, a step of separating its culture supernatant (medium after the culturing) or ascites.

The method for recovering the monoclonal antibody against dectin-1 from the culture is not particularly limited, too. For example, when the hybridoma of the present invention is cultured in a liquid medium and its culture supernatant (medium after the culturing) is used, the monoclonal antibody against dectin-1 can be recovered by collecting the culture supernatant (Medium after the culturing) by centrifugation, filtration or the like. Also, when the hybridoma of the present invention was cultured in the living body, the monoclonal antibody against dectin-1 can be recovered by collecting ascites or the like by a general method.

The cultured mixture, ascites or the like collected in this manner may be directly used as the monoclonal antibody against dectin-1, or further purified by a general antibody purification method.

Examples of the antibody purification method include salting out with sodium sulfate, ammonium sulfate or the like, low temperature alcohol precipitation, selective precipitation fractionation by polyethylene glycol or isoelectric point, elecrophoresis, ion exchange chromatography using an ion exchanger such as a DEAE (diethylaminoethyl)-derivative or CM (carboxymethyl)-derivative, affinity chromatography using protein A or protein G, hydroxyapatite chromatography, immunoadsorbent chromatography using immobilized antigen, gel filtration, ultracentrifugation and the like. In addition, these methods may be optionally combined.

Whether or not the antibody produced by the production process of the present invention binds to dectin-1, or whether or not it specifically binds thereto, and the like can be easily determined by those skilled in the art by general methods using dectin-1, other substance which becomes the antigen (e.g., other kind of protein) and the like.

<4> Detection Method of the Present Invention

The detection method of the present invention is a method for detecting dectin-1, which comprises reacting the antibody of the present invention with dectin-1.

In this connection, the term "detection" as used in the present application means to find out the substance of its object as a certain form. Accordingly, the term "detection" as used in the present application is a general idea which includes not only to find out the existence (presence or absence) of its detection object but also to quantitatively find out its detection object (to measure the detection object quantitatively). The method for reacting the antibody of the present invention with dectin-1 is not particularly limited, so long as it is carried out under such conditions that the molecule of the antibody of the present invention contacts with the molecule of dectin-1, and both of them are thereby bound to each other through the antigen-antibody reaction. Example of such conditions include conditions under which both of them are mixed and incubated at from 0° C. to 37° C. for 15 minutes to 2 hours.

Also, the antibody of the present invention to be reacted with dectin-1, or the dectin-1 to be reacted with the antibody of the present invention, may be in the state of being immobilized on a solid phase or the like. Accordingly, for example, detection of dectin-1 by immunoprecipitation using the antibody of the present invention, detection of dectin-1 by Western blotting using the antibody of the present invention, detection of dectin-1 on the cell surface by flow cytometry using the antibody of the present invention and the like are included in the detection method of the present invention.

In addition, it is not necessary to apply treatments such as isolation and purification in advance to the dectin-1 as the detection object. That is, according to the detection method of the present invention, dectin-1 can be specifically detected even when a component and the like other than dectin-1 are contained in the sample.

Dectin-1 can be detected by optionally selecting a conventionally known detection means in response to the kind or the like of the label bound to the antibody of the present invention. For example, when one substance of a specific binding pair (e.g., biotin) is used as the label, the other substance that specifically binds thereto (e.g., streptoavidin) conjugated with an enzyme (e.g., peroxidase or the like) is added to form the specific binding pair. Next, the substrate of the enzyme (e.g., hydrogen peroxide (when the enzyme is peroxidase)) and a coloring substance (e.g., 3,3',5,5'-tetramethylbenzidine, diaminobenzidine or the like) are added thereto, and the detection is effected by measuring the degree of coloration through absorbance caused by the product of the enzyme reaction.

Also, when a radioisotope, a fluorescence dye or a chemiluminescence substance, for example is used as the label, methods for measuring radioactivity counts, fluorescence intensity, fluorescence polarization, luminescence intensity, etc. and the like can be exemplified.

In addition, dectin-1 may be detected by labeling an antibody which binds to the antibody of the present invention (secondary antibody), and by using this.

According to the detection method of the present invention, dectin-1 can be detected via the detection and the like of such a label. When qualitative detection of dectin-1 (detection of the existence of dectin-1) is desired, the presence or absence of the detection of label can be directly used as the detection result. Also, when quantitative detection of dectin-1 (measurement of the concentration of dectin-1, or the like) is desired, absorbance, radioactivity counts, fluorescence intensity, luminescence intensity and the like can be used directly as the index of the amount of dectin-1. In addition, concentration and the like of dectin-1 in the sample can also be calculated by preparing a calibration curve or relational expression in advance using a standard solution of dectin-1 having known concentration, and by using this.

The detection method of the present invention may further comprise other steps, so long as it comprises at least the step of reacting the antibody of the present invention with dectin-1.

For example, it may further comprise not only a step in which the antibody of the present invention is allowed to react with dectin-1 and then dectin-1 is detected, but also a step in which one or both of the antibody of the present invention and dectin-1 are purified prior to their reaction, a step in which the solid phase or the like is washed after reacting the antibody of the present invention with dectin-1 and before detecting dectin-1, and the like.

EXAMPLES

The present invention is described below in more detail based on Examples.

Reference Example

Firstly, preparation methods of HEK 293 cell transfectant used in the example, which expresses mouse-derived dectin-1 (or a mutant thereof, and biotinylated SPG.

(1) Preparation of HEK 293 Cell Transfectant which Expresses Mouse-Derived Dectin-1 (or a Mutant Thereof)

A plasmid containing a cDNA encoding the mouse-derived dectin-1 (SEQ ID NO:1, GenBank accession number AF 262985) was amplified by a reverse transcriptase PCR from the total RNA prepared from a mouse macrophage cell line RAW 264 (obtained from RIKEN Cell Bank). The coding region of isoform A of this dectin-1 was inserted into a mammal expression vector p3xFLAG CMV-14 (manufactured by Sigma). This vector was converted into a linear chain and transfected into HEK 293 (obtained from Cell Resource Center for Biomedical Research, Tohoku University). Thereafter, a stable HEK 293 cell transfectant which expresses the mouse-derived dectin-1 was obtained by selecting it using a medium containing Geneticin (manufactured by Invitrogen).

An HEK 293 cell transfectant which expresses a mutant of the mouse-derived dectin-1 was produced in the following manner.

A plasmid of an amino acid-mutated dectin-1 mutant was constructed in the following manner by a PCR-mediated mutagenesis using KOD-Plus DNA polymerase (manufactured by TOYOBO) and DpnI nuclease (manufactured by Roche). Forward and reverse mutant oligonucleotide primers each containing 30 bases (manufactured by Sigma Genosys) were designed by replacing its 14th and/or 15th nucleotide residue by Ala code. An expression plasmid vector into which a wild type dectin-1 cDNA was inserted was faithfully reproduced by PCR using a KOD-Plus DNA polymerase and the above-described mutant oligonucleotide primers. The wild type dectin-1 cDNA was digested by incubating the template plasmid in the thus obtained PCR mixture at 37° C. for 3 hours in the presence of DpnI nuclease. The sense and antisense DNAs were mixed and transformed into *Escherichia coli* DH5α competent cells. DNA sequence of the plasmid having a mutation was confirmed using a DNA sequencer (ABI PRISM 310).

Thereafter, this cDNA having a mutation was inserted into the p3xFLAG CMV-14 vector, followed by transduction into the HEK 293 cell ($10^5$ cells/well) by lipofection using FuGene 6 (manufactured by Roche).

(2) Preparation of Biotinylated SPG

SPG was purchased from Kaken Pharmaceutical Co. Regarding the preparation of biotinylated SPG, it was prepared by the method described in *Biol. Pharm. Bull.*, 17, 1508-1512 (1994).

Example 1

Establishment of Hybridoma (1)

A soluble CRD of mouse-derived dectin-1 (sCRD; a peptide moiety which corresponds to the amino acids at position 119 to 244 in SEQ ID NO:2) was prepared from a culture supernatant of a CHO-dhfr⁻ transfectant (American Type Culture Collection). This cell line was prepared by electroporation using an expression vector containing a cDNA encoding the dectin-1 CRM and mouse dehydrofolate reductase.

Freund's complete adjuvant (manufactured by Difco) and sCRD were emulsified, followed by injection into the footpads of an F344 rat (obtained from Japan SLC). After completion of the third immunization, lymphocytes were collected by incising lymph node, fused with P3X63.Ag8.653 myeloma (obtained from Cell Resource Center for Biomedical Research, Tohoku University) and cultured under hypoxanthine, aminopterin and thymidine selection conditions.

Screening of an antibody-producing hybridoma was carried out by an enzyme-linked immunosorbent assay (ELISA) using a microplate coated with 5 μg/ml of sCRD. A hybridoma clone 4B2 which produces a rat immunoglobulin G2a/κ (IgG2a/κ) was obtained by carrying out selection of hybridoma by selecting a culture supernatant having activity of inhibiting binding of 5 μg/ml of biotinylated SPG and 2,000-fold diluted streptoavidin-linked peroxidase (manufactured by Pharmingen) to sCRD present on the microplate. This hybridoma clone (Mouse-Rat hybridoma 4B2) has been received on Oct. 22, 2004, as a deposit number FERM ABP-10151 by International Patent Organism Depositary, National Institute of Advanced Industrial Science and Technology, and deposited thereto as a deposit number FERM BP-10151. Hereinafter, this hybridoma clone and the antibody produced thereby are simply referred to as "4B2".

Example 2

Analysis of the Characteristics of 4B2 (1)

When SDS-PAGE was carried out on the soluble mouse-derived dectin-1 under non-reducing conditions and then Western blotting was carried out using 4B2, a band was detected at the position where the soluble mouse-derived dectin-1 was present. Based on this, it was shown that 4B2 binds to the mouse-derived dectin-1.

Example 3

Analysis of the Characteristics of 4B2 (2)

Transient transfectants ($3 \times 10^5$ cells) which express various mutant dectin-1 on the HEK 293 cell (obtained from Cell Resource Center for Biomedical Research, Tohoku University) were incubated on ice for 30 minutes in the presence of 4B2 or anti-FLAG BIO-M2 antibody (10 μg/ml; manufactured by Sigma). After washing the cells, biotinylated anti-rat IgG antibody (2.5 μg/ml) and streptoavidin-Alexa 488 (5 μg/ml; manufactured by Molecular Probes) were added thereto, followed by incubation on ice for 30 minutes, The resulting cells were washed, immobilized and analyzed by FACS. The results are shown in FIG. 1. The ordinate in respective histograms in FIG. 1 shows the number of cells, and the abscissa shows fluorescence intensity.

The graph of the uppermost row in FIG. 1 is a histogram respectively showing a result in which the HEK 293 cell transfected with a control vector was stained with 4B2, a result in which the HEK 293 cell transfected with wild type dectin-1 was stained with a control antibody, and a result in which the HEK 293 cell transfected with wild type dectin-1 was stained with 4B2. As a result, fluorescence intensity of the former two cases was low, while fluorescence intensity of the latter one was high, It was also shown from this result that 4B2 binds to the mouse-derived wild type dectin-1.

Also shown in FIG. 1 is a result of using HEK 293 cells respectively expressing "V220A" in which valine at position 220 in the dectin-1 molecule was mutated into alanine, "W221A" in which tryptophan at position 221 in the dectin-1 molecule was mutated into alanine, "I222A" in which isoleucine at position 222 was mutated into alanine, "H223A" in which histidine at position 223 was mutated into alanine, and "G224A" in which glycine at position 224 was mutated into alanine. In addition, the "W221A/I222A", "I222A/H223A" and "W221A/H223 A" show the results of using HEK 293 cells respectively expressing those which have these two respective mutations in the dectin-1 molecule. The shadowed histogram shows the result of staining with 4B2.

As a result, the staining with 4B2 was blocked in "W221A". In addition, the staining with 4B2 was also blocked in "W221A/I222A", "I222A/H223A" and "W221A/H223A" in the same manner. The staining with 4B2 was slightly blocked also in "I222A" and "H223A", but reduction of the staining with 4B2 was not found in the case of "V220A" and "G224A". From these results, it was shown that at least tryptophan at position 221 and its peripheral amino acid residues are essential for the binding of the 4B2 to dectin-1.

Example 4

Analysis of the Characteristics of 4B2 (3)

A transfectant of dectin-1 into which the FLAG tag was incorporated was incubated in advance on ice for 30 minutes in the presence of 1 mg/ml of SPG (available from Kaken Pharmaceutical Co.). Thereafter, a culture supernatant of 4B2 was added thereto, followed by incubation on ice for 30 minutes. Thereafter, the cells were washed, and the resulting cells were stained using biotinylated anti-rat IgG and streptoavidin-Alexa 488. The cells were washed, immobilized and analyzed by FACS. As a result, the binding of 4B2 to the SPG-treated transfectant was considerably decreased in comparison with the case in which the SPG treatment was not carried out. Contrary to this, when stained with streptoavidin-Alexa 488 using anti-FLAG BIO-M2 antibody instead of 4B2, the binding of anti-FLAG BIO-M2 antibody to the SPG-treated transfectant was not decreased.

In addition, a transfectant of dectin-1 into which the FLAG tag was incorporated was incubated in advance on ice for 30 minutes in the presence of 4B2. Thereafter, the cells were washed, and the resulting cells were stained using 1 μg/ml or 5 μg/ml of biotinylated SPG and streptoavidin-Alexa 488. The cells were washed, immobilized and analyzed by FACS. As a result, the binding of the biotinylated SPG to the 4B2-treated transfectant was considerably decreased in comparison with the case in which the 4B2 treatment was not carried out.

In addition, when dectin-1 was incubated in advance together with 4B2, the binding of dectin-1 to zymosan was inhibited depending on the concentration of 4B2.

Based on these results, it was suggested that the epitopes of the 4B2 and BG (SPG, zymosan or the like) in the dectin-1 molecule are common to each other.

Example 5

Establishment of Hybridoma (2)

After carrying out the same operation of Example 1, hybridomas was selected to obtain a hybridoma clone RH1 which produces a rat immunoglobulin G1/κ (IgG1/κ). This hybridoma clone (Mouse-Rat hybridoma RH1) has been received on Oct. 22, 2004, as a deposit number FERM ABP-10153 by International Patent Organism Depositary, National Institute of Advanced Industrial Science and Technology, and deposited thereto as a deposit number FERM BP-10153. Hereinafter, this hybridoma clone and the antibody produced thereby are simply referred to as "RH1".

Example 6

Analysis of the Characteristics of RH1 (1)

When SDS-PAGE was carried out on the soluble mouse-derived dectin-1 under non-reducing conditions and then Western blotting was carried out using RH1, a band was detected at the position where the soluble mouse-derived dectin-1 was present. Based on this, it was shown that RH1 binds to the mouse-derived dectin-1.

Example 7

Analysis of the Characteristics of RH1 (2)

Transfectants ($3 \times 10^5$ cells) which express dectin-1 on the HEK 293 cell (obtained from Cell Resource Center for Biomedical Research, Tohoku University) were incubated on ice for 30 minutes in the presence of RH1 or anti-FLAG BIO-M2 antibody (10 μg/ml; manufactured by Sigma). After washing the cells, biotinylated anti-rat IgG antibody (2.5 μg/ml) and streptoavidin-Alexa 488 (5 μg/ml; manufactured by Molecular Probes) were added thereto, followed by incubation on ice for 30 minutes. The resulting cells were washed, immobilized and analyzed by FACS As a result, the fluorescence intensity was low when anti-FLAG BIO-M2 antibody was used, while the fluorescence intensity was high when RH1 was used. It was also shown from this result that RH1 binds to the mouse-derived wild type dectin-1.

Example 8

Analysis of the Characteristics of RH1 (3)

A transfectant of dectin-1 into which the FLAG tag was incorporated was incubated in advance on ice for 30 minutes in the presence of 1 mg/ml of SPG (available from Kaken Pharmaceutical Co.). Thereafter, a culture supernatant of RH1 was added thereto followed by incubation on ice for 30 minutes. Thereafter, the cells were washed, and the resulting cells were stained using biotinylated anti-rat IgG and streptoavidin-Alexa 488. The cells were washed, immobilized and analyzed by FACS. As a result, the binding of RH1 to the SPG-treated transfectant was considerably decreased in comparison with the case in which the SPG treatment was not carried out. Contrary to this, when stained with streptoavidin-Alexa 488 using anti-FLAG BIO-M2 antibody instead of RH1, the binding of anti-FLAG BIO-M2 antibody to the SPG-treated transfectant was not decreased.

In addition, a transfectant of dectin-1 into which the FLAG tag was incorporated was incubated in advance on ice for 30 minutes in the presence of RH1. Thereafter, the cells were washed, and the resulting cells were stained using 1 μg/ml or 5 μg/ml of biofinylated SPG and streptoavidin-Alexa 488. The cells were washed, immobilized and analyzed by FACS. As a result, the binding of the biotinylated SPG to the RH1-treated transfecant was considerably decreased in comparison with the case in which the RH1 treatment was not carried out.

In addition, when dectin-1 was incubated in advance together with RH1, the binding of dectin-1 to zymosan was inhibited depending on the concentration of RH1.

Based on these results, it was suggested that the epitopes of the RH1 and BG (SPG, zymosan or the like) in the dectin-1 molecule are common to each other.

Example 9

Establishment of Hybridoma (3)

After carrying out the same operation of Example 1, hybridomas was selected to obtain a hybridoma clone SC30 which produces a rat immunoglobulin G2a/κ (IgG2a/κ). This hybridoma clone (Mouse-Rat hybridoma SC30) has been received on Oct. 22, 2004, as a deposit number FERM ABP-10152 by International Patent Organism Depositary, National Institute of Advanced Industrial Science and Technology, and deposited thereto as a deposit number FERM BP-10152. Hereinafter, this hybridoma clone and the antibody produced thereby are simply referred to as "SC30".

Example 10

Analysis of the Characteristics of SC30 (1)

When SDS-PAGE was carried out on the soluble mouse-derived dectin-1 under non-reducing conditions and then Western blotting was carried out using SC30, a band was detected at the position where the soluble mouse-derived dectin-1 was present. Based on this, it was shown that SC30 binds to the mouse-derived dectin-1.

Example 11

Analysis of the Characteristics of SC30 (2)

Transfectants ($3 \times 10^5$ cells) which express dectin-1 on the HEK 293 cell (obtained from Cell Resource Center for Biomedical Research, Tohoku University) were incubated on ice for 30 minutes in the presence of SC30 or anti-FLAG BIO-M2 antibody (10 μg/ml; manufactured by Sigma). After washing the cells, biotinylated anti-rat IgG antibody (2.5 μg/ml) and streptoavidin-Alexa 488 (5 μg/ml; manufactured by Molecular Probes) were added thereto, followed by incubation on ice for 30 minutes. The resulting cells were washed, immobilized and analyzed by FACS.

As a result, the fluorescence intensity was low when anti-FLAG BIO-M2 antibody was used, while the fluorescence intensity was high when SC30 was used. It was also shown from this result that SC30 binds to the mouse-derived wild type dectin-1.

Example 12

Analysis of the Characteristics of SC30 (3)

A transfectant of dectin-1 into which the FLAG tag was incorporated was incubated in advance on ice for 30 minutes in the presence of 1 mg/ml of SPG (available from Kaken Pharmaceutical Co.). Thereafter, a culture supernatant of SC30 was added thereto, followed by incubation on ice for 30 minutes. Thereafter, the cells were washed, and the resulting cells were stained using biotinylated anti-rat IgG and streptoavidin-Alexa 488. The cells were washed, immobilized and analyzed by FACS. As a result, the binding of SC30 to the SPG-treated transfectant was not decreased in comparison with the case in which the SPF treatment was not carried out. This was the same when stained with streptoavidin-Alexa 488 using anti-FLAG BIO-M2 antibody instead of SC30.

In addition, a transfectant of dectin-1 into which the FLAG tag was incorporated was incubated in advance on ice for 30 minutes in the presence of SC30. Thereafter, the cells were washed, and the resulting cells were stained using 1 μg/ml or 5 μg/ml of biotinylated SPG and streptoavidin-Alexa 488. The cells were washed, immobilized and analyzed by FACS. As a result the binding of the biotinylated SPG to the SC30-treated transfectant was not decreased in comparison with the case in which the SC30 treatment was not carried out.

In addition, when dectin-1 was incubated in advance together with SC30, the binding of dectin-1 to zymosan was not influenced by the concentration of SC30.

Based on these results, it was suggested that the epitopes of the SC30 and BG (SPG, zymosan or the like) in the dectin-1 molecule are not common to each other.

While the invention has been described in detail and with reference to specific embodiments thereof, it will be apparent to one skilled in the art that various changes and modifications can be made therein without departing from the spirit and scope thereof.

This application is based on Japanese patent application No. 2004-329795 filed on Nov. 12, 2004, Japanese patent application No. 2004-329796 filed on Nov. 12, 2004, and Japanese patent application No. 2004-329797 filed on Nov. 12, 2004, the entire contents of which are incorporated hereinto by reference.

INDUSTRIAL APPLICABILITY

The hybridoma of the present invention can be used as a production tool of an antibody against dectin-1. The antibody of the present invention can be used in the detection, measurement, affinity purification of dectin-1 and other applications. Also, the production process of the present invention can be used in the production of the antibody of the present invention. In addition, the detection method of the present invention can be used in the convenient and quick detection of dectin-1.

---

The invention claimed is:

1. A hybridoma deposited at International Patent Organism Depository, National Institute of Advanced Industrial Science and Technology, having deposit number FERM BP-10151, FERM BP-10152 or FERM BP-10153.

2. A monoclonal antibody against dectin-1, which is produced by the hybridoma according to claim 1.

3. A method for detecting dectin-1, which comprises contacting the monoclonal antibody according to claim 2 with a dectin-1 containing sample, and detecting binding of the monoclonal antibody to dectin-1 in the sample.

4. A process for producing a monoclonal antibody against dectin-1, which comprises culturing the hybridoma according to claim 1 and recovering the monoclonal antibody against dectin-1 from the culture.

* * * * *

SEQUENCE LISTING

```
<160> NUMBER OF SEQ ID NOS: 2

<210> SEQ ID NO 1
<211> LENGTH: 2298
<212> TYPE: DNA
<213> ORGANISM: Mus musculus
<220> FEATURE:
<221> NAME/KEY: CDS
<222> LOCATION: (89)..(823)
<223> OTHER INFORMATION:

<400> SEQUENCE: 1
gggtttggct tagtgagcct catcctggca gttattttac tagtaaagaa cattcaagtg      60
ctctgcctac ctagggccct gtgaagca atg aaa tat cac tct cat ata gag       112
                                Met Lys Tyr His Ser His Ile Glu
                                  1               5 aat ctg gat gaa gat gga tat act caa tta gac ttc agc act caa gac      160
Asn Leu Asp Glu Asp Gly Tyr Thr Gln Leu Asp Phe Ser Thr Gln Asp
     10                  15                  20 atc cat aaa agg ccc agg gga tca gag aaa gga agc cgg gct cca tct      208
Ile His Lys Arg Pro Arg Gly Ser Glu Lys Gly Ser Arg Ala Pro Ser
 25                  30                  35                  40 tca cct tgg agg ccc att gca gtg ggt tta gga atc ctg tgc ttt gtg      256
Ser Pro Trp Arg Pro Ile Ala Val Gly Leu Gly Ile Leu Cys Phe Val
                     45                  50                  55 gta gta gtg gtt gct gca gtg ctg ggt gcc cta gca ttt tgg cga cac      304
Val Val Val Val Ala Ala Val Leu Gly Ala Leu Ala Phe Trp Arg His
                 60                  65                  70 aat tca ggg aga aat cca gag gag aaa gac aac ttc cta tca aga aat      352
Asn Ser Gly Arg Asn Pro Glu Glu Lys Asp Asn Phe Leu Ser Arg Asn
             75                  80                  85 aaa gag aac cac aag ccc aca gaa tca tct tta gat gag aag gtg gct      400
Lys Glu Asn His Lys Pro Thr Glu Ser Ser Leu Asp Glu Lys Val Ala
```

```
              90                  95                100
ccc tcc aag gca tcc caa act aca gga ggt ttt tct cag tct tgc ctt    448
Pro Ser Lys Ala Ser Gln Thr Thr Gly Gly Phe Ser Gln Ser Cys Leu
105                 110                 115                 120 cct aat tgg atc atg cat ggg aag agc tgt tac cta ttt agc ttc tca    496
Pro Asn Trp Ile Met His Gly Lys Ser Cys Tyr Leu Phe Ser Phe Ser
                125                 130                 135 gga aat tcc tgg tat gga agt aag aga cac tgc tcc cag cta ggt gct    544
Gly Asn Ser Trp Tyr Gly Ser Lys Arg His Cys Ser Gln Leu Gly Ala
                140                 145                 150 cat cta ctg aag ata gac aac tca aaa gaa ttt gag ttc att gaa agc    592
His Leu Leu Lys Ile Asp Asn Ser Lys Glu Phe Glu Phe Ile Glu Ser
                    155                 160                 165 caa aca tcg tct cac cgt att aat gca ttt tgg ata ggc ctt tcc cgc    640
Gln Thr Ser Ser His Arg Ile Asn Ala Phe Trp Ile Gly Leu Ser Arg
            170                 175                 180 aat cag agt gaa ggg cca tgg ttc tgg gag gat gga tca gca ttc ttc    688
Asn Gln Ser Glu Gly Pro Trp Phe Trp Glu Asp Gly Ser Ala Phe Phe
185                 190                 195                 200 ccc aac tcg ttt caa gtc aga aat aca gtt ccc cag gaa agc tta ctg    736
Pro Asn Ser Phe Gln Val Arg Asn Thr Val Pro Gln Glu Ser Leu Leu
                205                 210                 215 cac aat tgt gta tgg att cat gga tca gag gtc tac aac caa atc tgc    784
His Asn Cys Val Trp Ile His Gly Ser Glu Val Tyr Asn Gln Ile Cys
                220                 225                 230 aat act tct tca tac agt atc tgt gag aag gaa ctg taa atgtatgtga    833
Asn Thr Ser Ser Tyr Ser Ile Cys Glu Lys Glu Leu
                235                 240 gaatataaag atggtgtgtg tgtgtgtgtg tgtgtgtgta catgcacaca caccaccacc    893
accaccacta ccaacaacag aacagaacag aacagaacag aacagaacag aacagattaa    953
tattaaaaaa cagaaaaaat gctgggatgc taagagactt taacctcatt tgagaacttg   1013
gatgaagaag ctgagacttt tgtacttgtc atcttcacaa agatggtggc actatcttcc   1073
agttaggaag tcactagaca tggagtgagg gcagctcaac aatacagaga atatgtgaac   1133
ctgaggtacc ctgactcaaa tttcacaacc acaatgaaac ccctacacta tcaggaaaca   1193
ctgtagagga gtgagactga agactttaaa agccagagaa tcagcctact tactgtggtg   1253
ttttctagac aggacaggga aagtatatct aggaaataaa aacaatacaa ttcagcaaac   1313
aaaatctgca taatgacaac ctcagttggt atggtatgtt atggtatggt atgggtgtag   1373
aagtttcaca aggccctatg aagaactaca gacagttaaa taggggaaaa gcttttttcta  1433
ggatcaagcc tactgaaccc caagaagtca gcactgaaca tatgtacaga tcagtatcat   1493
taaatgaact agtaagacat atacatatat gttaatcaaa tattggtacc agagtacaca   1553
ctgtgtttgc atgattttct cagtatctac agtacaccag acacagggag aaggcaaaat   1613
gaacttctaa attgagaagt gaaaaaaatg aggaaagaga atcttcacca caaatagggga  1673
ttctattttc acccacatga tcattattaa gatggccatc acccaaacgt cgtgacccaa   1733
gctacttcct caactagata actcaaagag tctgccacc ttttctgata gcaaatctgg    1793
tatctagatt tcactgtttc cttatgctgt ctggccagca gtatgacaaa ggtgctgccc   1853
tttcaggaag cagtctcctt aaatgctgta gttggaaaga taaatcatat ctgatagtga   1913
atatttaaaa agcgcccagt caggataagt gtttttggaac acagaacata ttycatcttt  1973
ttatgataca ctatcttgca attaacaacc aattcttaag tcatttcttt acaaacatat   2033
gactggaata tgactgtttc ctagtgtgat ctgtcttgtt aacttctaag attgtccatt   2093
```

-continued

```
aataccaccc ttatttccag tgtggacttc caaattgctg gggatctgtt tatagctttc    2153
tcagactaat caatatgtgg gcagaaattg tgctgagtcc actgaattgt tctcttgaaa    2213
atgattgggt ttatgtcact ttcatctcaa ttgaaaaact gcttattaaa gtatctttgg    2273
cctctgaaaa aaaaaaaaaa aaaaa                                          2298
```

<210> SEQ ID NO 2
<211> LENGTH: 244
<212> TYPE: PRT
<213> ORGANISM: Mus musculus

<400> SEQUENCE: 2

```
Met Lys Tyr His Ser His Ile Glu Asn Leu Asp Glu Asp Gly Tyr Thr
1               5                   10                  15

Gln Leu Asp Phe Ser Thr Gln Asp Ile His Lys Arg Pro Arg Gly Ser
            20                  25                  30

Glu Lys Gly Ser Arg Ala Pro Ser Ser Pro Trp Arg Pro Ile Ala Val
        35                  40                  45

Gly Leu Gly Ile Leu Cys Phe Val Val Val Val Ala Ala Val Leu
    50                  55                  60

Gly Ala Leu Ala Phe Trp Arg His Asn Ser Gly Arg Asn Pro Glu Glu
65                  70                  75                  80

Lys Asp Asn Phe Leu Ser Arg Asn Lys Glu Asn His Lys Pro Thr Glu
                85                  90                  95

Ser Ser Leu Asp Glu Lys Val Ala Pro Ser Lys Ala Ser Gln Thr Thr
            100                 105                 110

Gly Gly Phe Ser Gln Ser Cys Leu Pro Asn Trp Ile Met His Gly Lys
        115                 120                 125

Ser Cys Tyr Leu Phe Ser Phe Ser Gly Asn Ser Trp Tyr Gly Ser Lys
    130                 135                 140

Arg His Cys Ser Gln Leu Gly Ala His Leu Leu Lys Ile Asp Asn Ser
145                 150                 155                 160

Lys Glu Phe Glu Phe Ile Glu Ser Gln Thr Ser Ser His Arg Ile Asn
                165                 170                 175

Ala Phe Trp Ile Gly Leu Ser Arg Asn Gln Ser Glu Gly Pro Trp Phe
            180                 185                 190

Trp Glu Asp Gly Ser Ala Phe Phe Pro Asn Ser Phe Gln Val Arg Asn
        195                 200                 205

Thr Val Pro Gln Glu Ser Leu Leu His Asn Cys Val Trp Ile His Gly
    210                 215                 220

Ser Glu Val Tyr Asn Gln Ile Cys Asn Thr Ser Ser Tyr Ser Ile Cys
225                 230                 235                 240

Glu Lys Glu Leu
```